United States Patent [19]
Coccia
[11] Patent Number: 4,909,290
[45] Date of Patent: Mar. 20, 1990

[54] SAFETY DEVICE FOR FILLING LIQUIDS IN DRUG BOTTLES AND DRAWING SAID LIQUIDS THEREFROM

[75] Inventor: Mario Coccia, Cesano Boscone, Italy
[73] Assignee: Farmitalia Carlo Erba S.R.L., Milan, Italy

[21] Appl. No.: 246,093
[22] Filed: Sep. 19, 1988
[30] Foreign Application Priority Data
Sep. 22, 1987 [IT] Italy .............................. 22404/87[U]
[51] Int. Cl.[4] .......................... B65B 3/04; A61M 5/00
[52] U.S. Cl. .................................. 141/329; 604/905; 604/411; 604/198; 141/383; 141/387
[58] Field of Search .................... 141/329, 330, 25–27, 141/383–386, 387–389; 604/407, 411–415, 905, 198, 201, 204

[56] References Cited
U.S. PATENT DOCUMENTS 3,820,542 6/1974 Hurschman .......................... 604/201
4,161,949 7/1979 Thanawalla .................... 604/905 X
4,180,070 12/1979 Genese ............................ 604/414 X
4,191,225 3/1980 Ogle .................................... 141/329
4,196,732 4/1980 Wardlaw ........................ 141/330 X
4,564,054 1/1986 Gustavsson .......................... 141/329
4,576,211 3/1986 Valentini et al. .................. 141/329
4,589,879 5/1986 Pearson ............................... 604/411
4,619,651 10/1986 Kopfer et al. ....................... 604/415
4,737,150 4/1988 Baeumle et al. .................... 604/198
4,768,568 9/1988 Fournier et al. .................... 141/286

*Primary Examiner*—Ernest G. Cusick
*Attorney, Agent, or Firm*—Oblon, Spivak, McClelland, Maier & Neustadt

[57] ABSTRACT

The device includes a syringe and an apparatus for coupling the syringe to a drug holding bottle and the like, the apparatus defining an enclosed chamber wherein there is housed a needle to be coupled to the syringe and the free end of which is arranged is front of a tightness resilient member located at a seat adapted to receive the mouth of the bottle, the syringe being firmly and fixedly clamped, in a tight way, in a syringe seat formed in the apparatus.

3 Claims, 1 Drawing Sheet

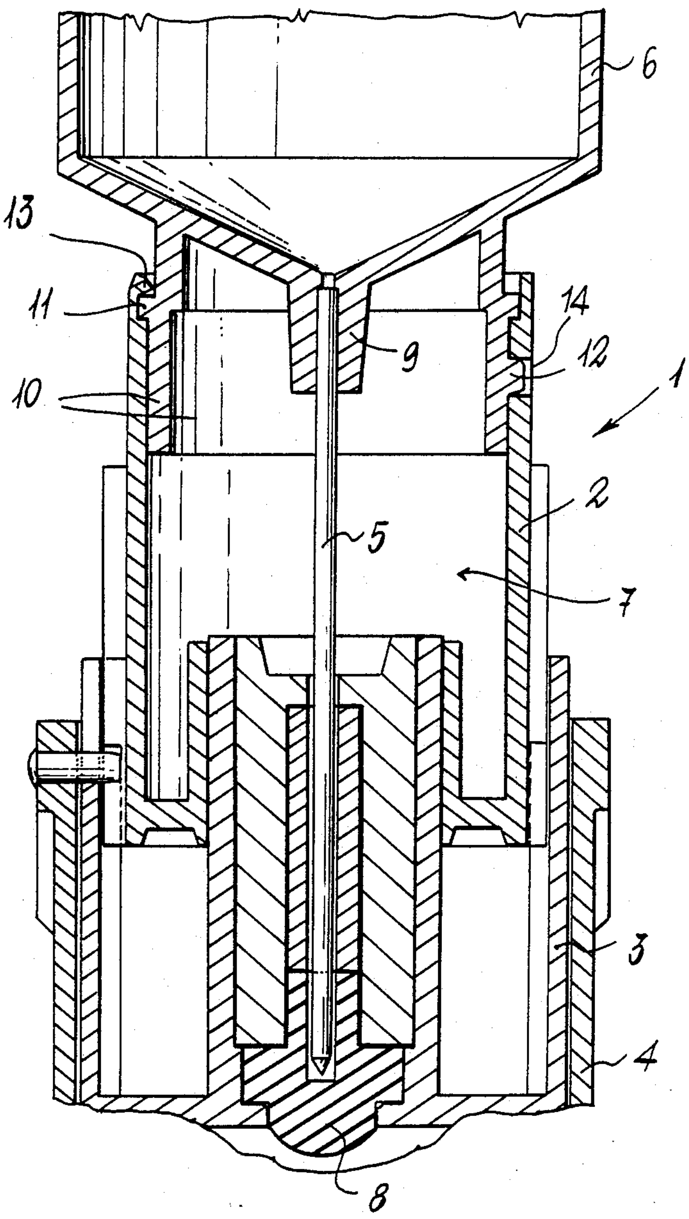
6
13
11
14
9
12
1
10
2
5
7
3
4
8

SAFETY DEVICE FOR FILLING LIQUIDS IN DRUG BOTTLES AND DRAWING SAID LIQUIDS THEREFROM

The present invention relates to a safety device for filling liquids in drug bottles and drawing the filled in liquids therefrom.

As is known, drugs are conventionally enclosed in bottles the inlets of which are closed by plug members which can be perforated by using the needle of a syringe:as the drug is in the liquid state it can be directly drawn into the syringe through its needle whereas, as the drug is in powder form, it is necessary to introduce (by the syringe needle) a suitable solvent into said bottle and then draw the formed solution therefrom.

In some cases the drug bottles contain very toxic, polluting and dangerous drugs, such as anti-tumor drugs: in this case particular apparatus and precautions must be used and applied in order to prevent the operator from being contaminated by the liquid which may drip from the syringe needle as it is withdrawn from the bottle plug or during the transfer to the patient of the drug holding syringe.

To that end, apparatus have been designed which can be coupled to the syringes and comprise an enclosed chamber housing a needle which can be withdrawn therefrom exclusively as the apparatus is firmly engaged on the bottle mouth:such an apparatus is disclosed in U.S. Pat. No. 4,576,211.

In this patent the coupling of the syringe to the apparatus is of the reversible type, that is the syringe may also be detached from the apparatus.

Thus, because of inattention or erroneous handling by the operator, the syringe may be detached from the related apparatus as the syringe already contains the drug, which would be very dangerous.

Moreover, since the coupling of the syringe to the apparatus is directly performed by the operator, the possibility exists that, because of an imperfect coupling, liquid may leak or the syringe may be detached from the apparatus.

SUMMARY OF THE INVENTION

Accordingly, the main object of the present invention is to overcome the above mentioned drawbacks by providing a device, consisting of an apparatus of the above mentioned type and a syringe in which the syringe is firmly and fixedly tightly coupled to said apparatus.

According to one aspect of the invention this and other objects are achieved by a device comprising a syringe and an apparatus defining a closed chamber tightly housing a movable needle the tip of which can be withdrawn from the chamber exclusively as the apparatus is firmly engaged on the mouth of a bottle to which the apparatus is connected by means of gripping members included in the apparatus, the device being characterized in that the syringe is tightly, firmly and fixedly clamped in a respective seat provided in the apparatus.

BRIEF DESCRIPTION OF THE DRAWING

The invention will become more apparent hereinafter from the following description of a preferred embodiment with reference to the accompanying drawing the SOLE FIGURE of which is a partial cross-sectional view of the subject device.

DESCRIPTION OF THE PREFERRED EMBODIMENT

The device shown in the drawing comprises an apparatus 1 which includes members (not shown for simplicity and since they can be made in different ways) for clamping said apparatus, under safety conditions, on the inlet or mouth or a drug containing bottle or the like.

The apparatus 1, in turn, comprises an inner body 2, a middle body 3 and an outer body 4 which are coupled to one another and can be axially displaced with respect to one another between two ends of stroke elements at one of which a needle 5 connected to a syringe 6 is completely protected in a closed chamber or bore which, at the bottom, is closed by a rubber or the like plug 8. At the other end of stroke element, the needle 5 perforates the plug 8 and projects thereunder, whereas the apparatus 1 remains firmly anchored on the drug holding bottle (not shown).

The structure of the apparatus 1 is well known per se and is not described in any further detail herein; an embodiment of this apparatus is shown in the U.S. Pat. No. 4,576,211 but it should be apparent that the apparatus can be designed in an equivalent way.

As shown in the drawing, the top portion of the inner body 2 is formed as a cylindrical wall 7 in which recesses 14 are formed, as shown in the drawing. From the syringe, about the overall extension of the needle 5 and bearing lug 9, a tubular wall 10 extends, which is tightly enclosed in the space defined by the cylindrical wall of the body 2, whereas shaped projections 11,12 which project from the outer surface of the tubular wall 10 are housed and force fitted in the mentioned recesses formed in the cylindrical wall of the body 2.

The free edge of the cylindrical wall of the body 2 is firmly deformed in a suitable way (e.g. by thermal deformation) so as to form one or more teeth or rims 13 adapted to clamp and firmly hold the projection 11. The cylindrical wall 7 forming a syringe seat in which the syringe 6 is fixedly clamped.

Thus the syringe 6 will be firmly anchored to the apparatus 1, provides a perfect tightness thereon, and is non-removably coupled so that the syringe cannot be removed therefrom without breaking at least the rims 13.

The device can be used as disclosed in the U.S. Pat. No. 4,576,211 and for simplicity the use procedure is not discussed herein.

I claim:

1. A safety device adapted to be connected to an opening of a bottle comprising:
   - a syringe comprising a movable needle, said needle having a tip at its lower end, said syringe further comprising a tubular wall projecting from the syringe and surrounding an upper end of said needle, wherein projections are formed on an exterior surface of said tubular wall; and
   - an apparatus defining an enclosed chamber for housing said movable needle, said tip of said movable needle being positionable to a position beyond said chamber when said device is connected to said bottle, said apparatus further defining a cylindrical wall projecting from said chamber and comprising recesses formed at its upper end, said tubular wall being forcefitted into said cylindrical wall into a position in which said projections are force-fitted into said recesses;

wherein said syringe is non-removably coupled to said apparatus.

2. A safety device according to claim 1, wherein said apparatus comprises:

an inner body, a middle body and an outer body, said cylindrical wall defining said inner body, said inner body being non-removably coupled to said syringe, said inner body being housed within said middle body and said middle body being housed within said outer body, said inner body, middle body and outer body being coupled to one another with said inner body being axially displacable with respect to said middle body and said outer body;

wherein said inner body is movable with respect to said middle body and said outer body from a position in which said movable needle is housed within said chamber to said position in which said tip of said needle is disposed beyond said chamber.

3. A safety device according to claim 1, wherein a free edge of said cylindrical wall forms a rim at its upper end, said rim being adapted to restrain at least one of said projections.

* * * * *